United States Patent
Lopera

(10) Patent No.: US 8,232,890 B2
(45) Date of Patent: Jul. 31, 2012

(54) GUIDANCE SYSTEM AND METHOD FOR MEDICAL PROCEDURES

(75) Inventor: Jorge Lopera, San Antonio, TX (US)

(73) Assignee: The Board of Regents of The University of Texas System, Austin, TX (US)

(*) Notice: Subject to any disclaimer, the term of this patent is extended or adjusted under 35 U.S.C. 154(b) by 369 days.

(21) Appl. No.: 12/501,956

(22) Filed: Jul. 13, 2009

(65) Prior Publication Data
US 2010/0013655 A1 Jan. 21, 2010

Related U.S. Application Data

(60) Provisional application No. 61/082,006, filed on Jul. 18, 2008.

(51) Int. Cl.
*G08B 21/00* (2006.01)
(52) U.S. Cl. ............... 340/686.1; 604/116
(58) Field of Classification Search ........... 340/686.1; 600/427, 567, 566; 128/989, 303 B, DIG. 26; 604/108, 116
See application file for complete search history.

(56) References Cited

U.S. PATENT DOCUMENTS

| 4,733,661 | A | 3/1988 | Palestrant | 128/999.999 |
| 4,930,525 | A | 6/1990 | Palestrant | 128/898 |
| 7,204,826 | B2* | 4/2007 | Tremaglio et al. | 604/164.12 |
| 7,484,305 | B2* | 2/2009 | Sherry et al. | 33/391 |
| 7,771,437 | B2* | 8/2010 | Hogg et al. | 606/130 |
| 7,824,417 | B2* | 11/2010 | Magnusson et al. | 606/130 |
| 2007/0149878 | A1* | 6/2007 | Hankins | 600/427 |

OTHER PUBLICATIONS

Chakeres et al., "Real-time CT-guided spinal biopsy with a disposable stereotactic device: a technical note," *Am. J. Neuroradiol.*, 23: 605-608, 2002.
Fichtinger, "CT-guided percutaneous spinal injections," Course Notes for 'Introduction of computer integrated surgery,' Johns Hopkins University, 1999-2007.

* cited by examiner

*Primary Examiner* — Toan N Pham
(74) *Attorney, Agent, or Firm* — Fulbright & Jaworski L.L.P.

(57) ABSTRACT

Embodiments of the present invention comprise a guidance system and method for providing an angular orientation of a medical device. The system and method may utilize a fluid-filled portion with a position indicator that floats in the fluid contained within the fluid-filled portion. The guidance system may be coupled to the medical device so that when the angular orientation of the guidance system is varied, the position indicator moves within the fluid-filled portion. The position of the position indicator is designated by angle gradations on the outer portion of the fluid-filled portion.

14 Claims, 2 Drawing Sheets

GUIDANCE SYSTEM AND METHOD FOR MEDICAL PROCEDURES

CROSS-REFERENCE TO RELATED APPLICATIONS

This application claims priority to U.S. Provisional Patent Application No. 61/082,006 filed on Jul. 18, 2008, the disclosure of which is herein incorporated by reference.

BACKGROUND OF THE INVENTION

I. Field of the Invention

The present invention relates generally to the fields of a guidance system for medical procedures. Specific embodiments relate to hand-held guidance systems and methods for procedures such as computed tomography-guided procedures.

II. Description of Related Art

Current guidance systems for medical procedures include systems that are quite complex and expensive, such as laser guided systems. Current systems also include systems that only provide indications of the orientation of medical equipment in one plane.

Therefore, there remains a need for a cost-efficient guidance system configured to provide the orientation of medical equipment in more than one plane.

SUMMARY OF THE INVENTION

Embodiments of the present invention comprise a guidance system and method for providing an angular orientation of a medical device. The system and method may utilize a fluid-filled portion with a position indicator that floats in the fluid contained within the fluid-filled portion. The guidance system can be coupled to the medical device so that when the angular orientation of the guidance system is varied, the position indicator moves within the fluid-filled portion.

The location of the position indicator is designated by angle gradations on the outer portion of the fluid-filled portion. The angle gradations can provide the orientation of the system in relation to two separate reference planes. The position indicator can be any suitable device that is capable of floating in the fluid. Non-limiting examples of position indicators include floating balls or bubbles in the fluid. The angle gradations can be provided in any increment desired, including for example, increments of 45, 40, 35, 30, 25, 20, 15, 10, 5, 4, 3, 2, or 1 degree, or any increment between these values.

The fluid-filled portion may be filled with any suitable fluid, including for example water or a saline solution. The fluid-filled portion may be contained within a shell or housing that allows a user to see the position indicator contained within the housing. In certain embodiments, the housing may be transparent or translucent. The housing may also be comprised of a material that is resistant to breaking, such as a high impact plastic, should the guidance system be accidentally dropped.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The following drawings form part of the present specification and are included to further demonstrate certain aspects of the present invention. The drawings do not limit the scope but simply offer examples. The invention may be better understood by reference to one or more of these drawings in combination with the description of the illustrative embodiments presented herein.

DESCRIPTION OF ILLUSTRATIVE EMBODIMENTS

The invention and the various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only and not by way of limitation. Various substitutions, modifications, additions, and/or rearrangements within the spirit and/or scope of the underlying inventive concept will become apparent to those skilled in the art from this disclosure.

Figure 1:
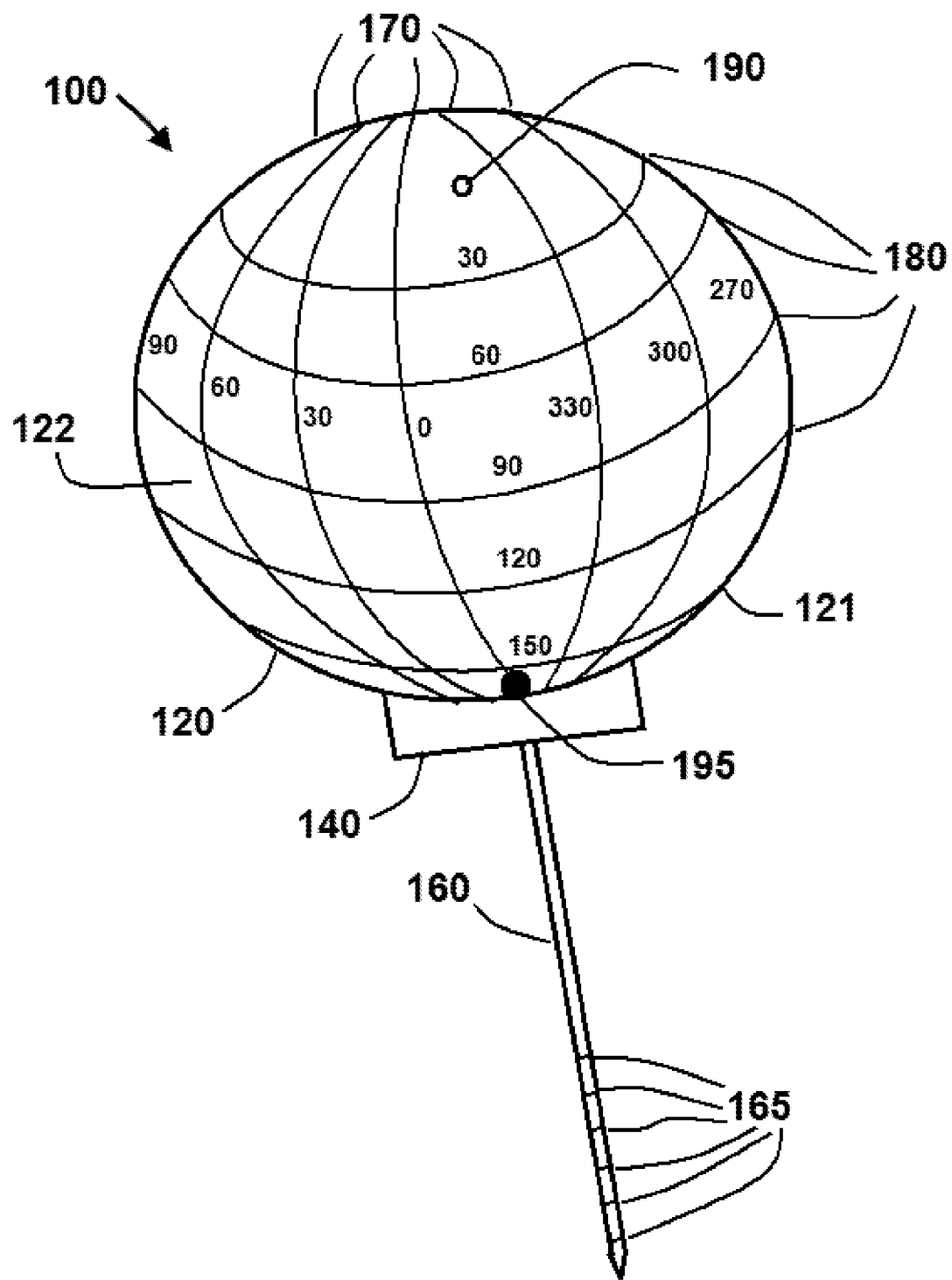
FIG. 1 is a perspective view of a guidance system according to exemplary embodiments of the present invention.
Figure 2:
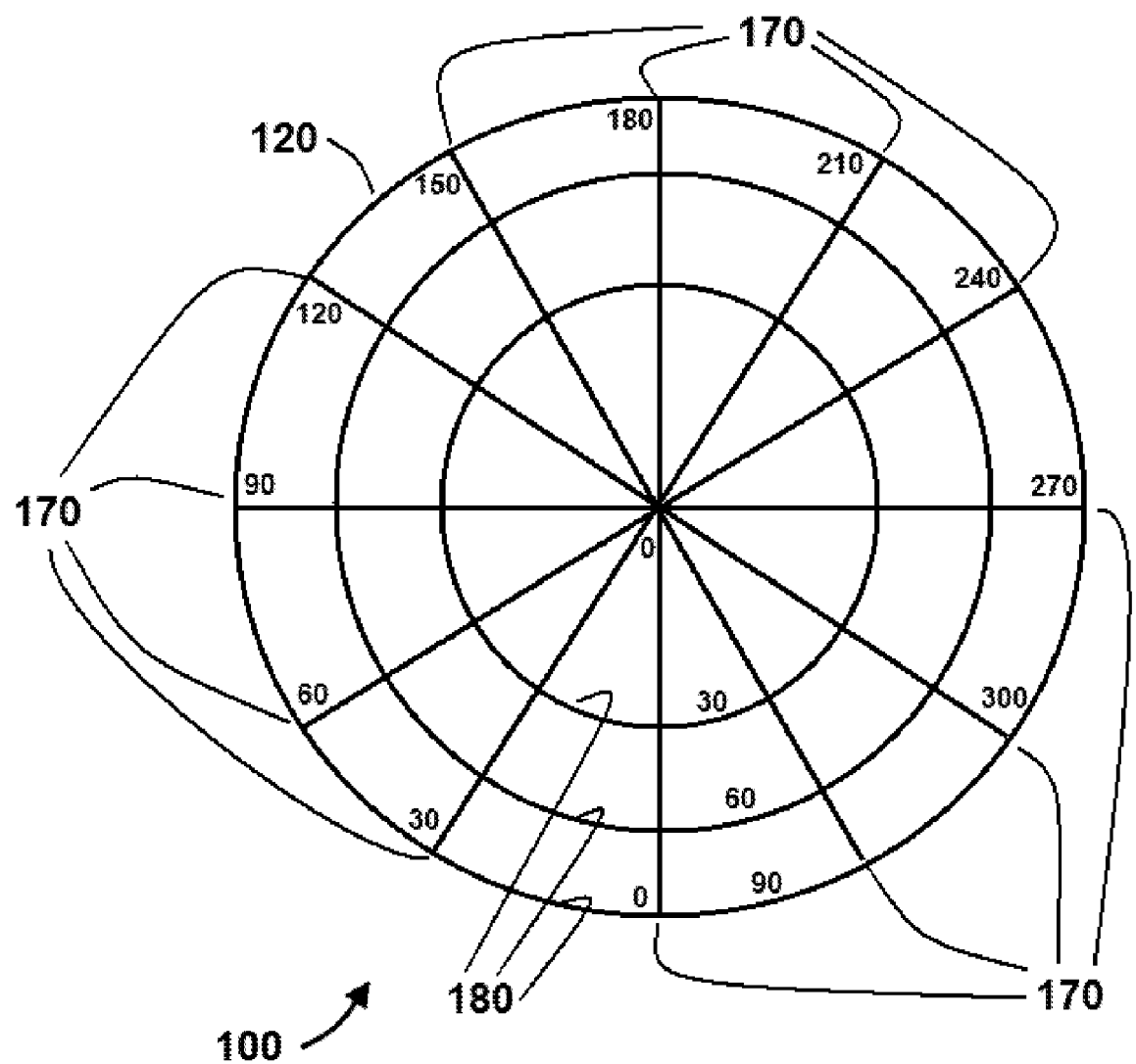
FIG. 2 is top view of the embodiment of FIG. 1.

Referring initially to FIG. 1, a guidance system or device 100 comprises a fluid-filled portion 120, a retention mechanism 140, and a needle 160. Fluid-filled portion 120 comprises an outer housing 121 containing a fluid 122 and a position indicator 190 configured to float within fluid 122. In certain embodiments, position indicator 190 may be a bubble within fluid 122, while in other embodiments, position indicator may be a floating device such as a ball made from a material with a density that is less than fluid 122.

In the embodiment shown, outer housing 121 comprises a first set of markers or angle gradations 170 and a second set of markers or angle gradations 180. In this embodiment, first set of angle gradations 170 are configured to provide an indication of the orientation of guidance device 100 with respect to a first plane (e.g., a vertical plane, not shown) by examining the spatial relationship between position indicator 190 and angle gradations 170. In certain embodiments, an illumination source 195 (e.g. a light bulb) can illuminate a portion of guidance device 100 so that the location of position indicator 190 can be more easily determined. In specific embodiments, illumination source 195 may be contained within fluid-filled portion 120. In the embodiment shown, second set of angle gradations 180 are configured to provide an indication of the orientation of guidance device 100 with respect to a second plane (e.g., a horizontal plane) by examining the spatial relationship between position indicator 190 and angle gradations 180. It is understood that angle gradations 170, 180 may be provided in any increment desired. However, the embodiment shown in FIG. 1 has illustrated only 30 degree increments for purposes of clarity.

In the embodiment shown, needle 160 is detachable from retention mechanism 140; however, it is understood that needle 160 may or may not be integral with guidance device 100. In certain embodiments, retention mechanism 140 may be configured as a clamp, a retaining clip, a slot, or any other configuration suitable for retaining needle 160. In exemplary embodiments, retention mechanism 140 is configured to retain different types and/or sizes of needles or medical devices so that guidance device 100 may be used in different types of procedures.

In certain exemplary embodiments, needle 160 can be removed and disposed, while fluid-filled portion 120 is reused. Fluid-filled portion 120 (as well as other portions of guidance system 100) may be packaged in sterile packaging, and/or may be robust enough to withstand sterilization before and after use. In certain embodiments, needle 160 and fluid-filled portion 120 may both be disposable so that the entire guidance device 100 is disposed after each use. In embodiments in which needle 160 can be separated from fluid-filled portion 120 (as well as embodiments in which needle 160 is integral with fluid-filled portion 120) retention mechanism 140 secures needle 160 so that needle 160 is fixed relative to fluid-filled portion 120. Therefore, determining the position or angular orientation of fluid-filled portion 120 (via position indicator 190 and angle gradations 170, 180) also allows a user to determine the position or angular orientation of needle 160.

In exemplary embodiments, retention mechanism 140 secures needle 160 in a position so that when needle 160 is held in a vertical position (e.g., needle 160 is pointed towards the center of the earth), position indicator 190 is proximal to angle gradations 170, 180 that each indicate 0 degrees of inclination for needle 160. Guidance device 100 can be used to determine the angular orientation of needle 160 in the following exemplary manner. A user may grasp fluid-filled portion 120 and tilt guidance device 100 until position indicator 190 is located proximal to a desired angle gradation 180. As guidance device 100 is tilted, position indicator 190 will remain at or near the uppermost portion of fluid-filled portion 120 (with the uppermost portion of fluid-filled portion 120 being the portion that is farthest from the gravitational pull of the earth). Therefore, as guidance device 100 is tilted or rotated with respect to a horizontal reference plane, different angle gradations 180 are positioned at the uppermost portion of fluid-filled portion 120. Position indicator 190 will therefore be proximal to different angle gradations 180 as guidance device 100 is tilted or rotated in this manner. Angle gradations 180 can be marked to provide an indication of the angle of needle 160 relative to a horizontal reference plane. For example, guidance device 100 can be tilted so that position indicator 190 is proximal to an angle gradation 180 that is marked "30". This indicates that guidance device 100 has been tilted so that needle 160 is positioned at an angle of approximately 30 degrees from a horizontal reference plane.

Similarly, guidance device 100 can be moved with respect to a vertical reference plane. As guidance device is moved in such a manner, position indicator 190 will become proximal to different angle gradations 170. Position indicator 190 will therefore indicate the orientation of needle 160 with respect to a vertical reference plane, as well as a horizontal reference plane. For example, guidance device 100 can be tilted so that position indicator 190 is proximal to a desired angle gradation 170. For example, guidance device 100 can be tilted so that position indicator 190 is proximal to an angle gradation 170 that is marked "30". This indicates that guidance device 100 has been tilted so that needle 160 is positioned at an angle of approximately 30 degrees to a vertical reference plane.

Guidance device 100 can be used to provide a user with an accurate and efficient method of determining the angle of needle 160 (or another medical device) during a medical procedure, e.g. a biopsy, drainage, or radio frequency ablation. Guidance device 100 can be used to assist a user in avoiding tissue that the user does not want to disturb and to target tissue that the user would like to reach with needle 160.

In certain examples, needle 160 (or another medical device) may include distance indications 165 that indicate the distance from the tip of needle 160. Distance indications 165 can provide a user with an indication of how far a medical device has been inserted into a patient. A user can therefore orient needle 160 at a desired first angle and insert needle 160 a desired first amount, and then orient needle 160 at a desired second angle and continue inserting needle 160 further into the patient. Such a system and method may be useful to avoid puncturing tissue that is proximal to the surface with the tip of needle 160.

All of the systems, devices and/or methods disclosed and claimed herein can be made and executed without undue experimentation in light of the present disclosure. While the systems, devices and methods of this invention have been described in terms of particular embodiments, it will be apparent to those of skill in the art that variations may be applied to the systems, devices and/or methods in the steps or in the sequence of steps of the method described herein without departing from the concept, spirit and scope of the invention. For example, while a needle has been shown in the exemplary embodiment, other medical devices, such as probes or scopes may be used instead of, or in conjunction with, the needle. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Pat. No. 4,733,661
U.S. Pat. No. 7,277,594
U.S. Pat. No. 6,853,856
U.S. Pat. No. 6,030,348
U.S. Pat. No. 6,013,035

U.S. Pat. No. 5,957,933
U.S. Pat. No. 5,628,327
U.S. Pat. No. 5,575,798
U.S. Pat. No. 5,314,432
U.S. Pat. No. 5,308,352
U.S. Pat. No. 5,242,455
U.S. Pat. No. 5,102,391
U.S. Pat. No. 5,047,036
U.S. Pat. No. 4,930,525
U.S. Patent App. Pub. No. 20080057505
U.S. Patent App. Pub. No. 20080051644
U.S. Patent App. Pub. No. 20070149878
U.S. Patent App. Pub. No. 20070060507
U.S. Patent App. Pub. No. 20060046259
U.S. Patent App. Pub. No. 20050080333
U.S. Patent App. Pub. No. 20050033315
U.S. Patent App. Pub. No. 20050032693
U.S. Patent App. Pub. No. 20040077090

What is claimed:

1. A guidance system comprising:
an outer housing;
a fluid contained within the outer housing;
a position indicator;
a plurality of angle gradations on the outer housing; and
a medical device retention mechanism, wherein:
the plurality of angle gradations comprise a first plurality of angle gradations configured to provide an indication of the angle of the guidance system with respect to a horizontal plane; and
the plurality of angle gradations comprise a second plurality of angle gradations configured to provide an indication of the angle of the guidance system with respect to a vertical plane.

2. The guidance system of claim 1, wherein a density of the position indicator is less than the density of the fluid.

3. The guidance system of claim 1, further comprising a needle coupled to the medical device retention mechanism.

4. The guidance system of claim 1, wherein the outer housing is spherical.

5. The guidance system of claim 1, further comprising an illumination source.

6. The guidance system of claim 1, wherein the position indicator is a bubble in the fluid.

7. The guidance system of claim 1, wherein the position indicator is a floating ball.

8. The guidance system of claim 1, wherein the medical device retention mechanism comprises a clamp.

9. The guidance system of claim 1, wherein the outer housing is transparent.

10. The guidance system of claim 1, wherein the outer housing is translucent.

11. A method of determining an angular orientation of a medical device, the method comprising:
providing an outer housing;
providing a fluid within the outer housing;
providing a position indicator floating in the fluid;
providing a plurality of angle gradations on the outer housing, wherein the plurality of angle gradations comprise a first plurality of angle gradations configured to provide an indication of the angle of the guidance system with respect to a horizontal plane and the plurality of angle gradations comprise a second plurality of angle gradations configured to provide an indication of the angle of the guidance system with respect to a vertical plane;
coupling a medical device to the outer housing; and
orienting the outer housing so that the position indicator is proximal to a desired angle gradation.

12. The method of claim 11, further comprising inserting the medical device into a patient when the position indicator is proximal to the desired angle gradation.

13. The method of claim 11, further comprising performing a biopsy with the medical device when the position indicator is proximal to the desired angle gradation.

14. The method of claim 11, wherein the medical device is a needle.

* * * * *